(12) United States Patent
Butler et al.

(10) Patent No.: US 8,021,394 B2
(45) Date of Patent: Sep. 20, 2011

(54) STENOTIC DEVICE

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 262 days.

(21) Appl. No.: 11/801,291

(22) Filed: May 9, 2007

(65) Prior Publication Data
US 2007/0276381 A1 Nov. 29, 2007

Related U.S. Application Data

(60) Provisional application No. 60/798,894, filed on May 9, 2006.

(51) Int. Cl.
*A61B 17/70* (2006.01)
*A61F 2/44* (2006.01)
(52) U.S. Cl. .................. 606/249; 606/248; 623/17.11
(58) Field of Classification Search .......... 606/248–249; 623/17.11–17.16
See application file for complete search history.

(56) References Cited

U.S. PATENT DOCUMENTS

| | | | | |
|---|---|---|---|---|
| 2,677,369 | A * | 5/1954 | Knowles | 606/249 |
| 5,011,484 | A * | 4/1991 | Breard | 606/249 |
| 5,496,318 | A * | 3/1996 | Howland et al. | 606/249 |
| 5,836,948 | A | 11/1998 | Zucherman et al. | |
| 6,582,433 | B2 | 6/2003 | Yun | |
| 6,626,944 | B1 | 9/2003 | Taylor | |
| 6,761,720 | B1 * | 7/2004 | Senegas | 606/249 |
| 6,946,000 | B2 * | 9/2005 | Senegas et al. | 623/17.11 |
| 2002/0116000 | A1 * | 8/2002 | Zucherman et al. | 606/61 |
| 2006/0224159 | A1 * | 10/2006 | Anderson | 606/61 |
| 2006/0241614 | A1 * | 10/2006 | Bruneau et al. | 606/69 |

FOREIGN PATENT DOCUMENTS
WO WO 2007/133608 A2 11/2007

OTHER PUBLICATIONS

International Search Report for Application No. PCT/US07/11251, date of mailing Sep. 22, 2008, 1 page.
Written Opinion of the International Searching Authority for Application No. PCT/US07/11251, date of mailing Sep. 22, 2008, 3 pages.

* cited by examiner

*Primary Examiner* — Eduardo C Robert
*Assistant Examiner* — Julianna N Harvey
(74) *Attorney, Agent, or Firm* — Foley & Lardner LLP

(57) ABSTRACT

A spinal implant is configured to be received between bony spinal protrusions of adjacent vertebrae particularly, but not necessarily, in the lumbar region of the spine and hold them apart. The spinal implant may be used interlaminar, interbody or interbony protrusion. The present bony spinal protrusion spacer is not fixed to any bony structures of the vertebrae and, as such, use of the present bony spinal protrusion spacer does not result in fusion. It may therefore be removed if necessary. Attachment structures formed as part of the bony spinal protrusion spacer receive and engage portions of adjacent bony protrusions. The attachment structures provide one or more ridges, bumps, protrusions, projections, lips, flanges, overhangs, overhangs that are threadably engaged, extensions and/or the like that form one or more pockets or cavities into which portions of adjacent bony spinal protrusions are separately lodged and held. In this manner (via retention of the bony spinal protrusions), appropriate and/or desired spacing between adjacent vertebrae is maintained. As such, the present bony spinal protrusion spacer is designed to remain safely and permanently in place without attaching to the bone or ligaments of the back.

11 Claims, 4 Drawing Sheets

STENOTIC DEVICE

RELATED APPLICATIONS

This patent application claims the benefit of and/or priority to U.S. Provisional Patent Application No. 60/798,894 filed May 9, 2006, entitled "Interspinous Process Spacer" the entire contents of which is specifically incorporated herein by reference.

BACKGROUND OF THE INVENTION

1. Field of the Invention

The present invention relates to devices for the spine and, more particularly, to a spinal implant for the treatment of stenotic spinal bone.

2. Background Information

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as lumbar spinal stenosis. Lumbar spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of lumbar spinal stenosis include leg pain ("pins and needles") that can limit standing, walking, self-supporting daily activities, work social and recreational pursuits. Lack of activity because of lumbar spinal stenosis may lead to obesity, depression and general physical deterioration.

Once diagnosed with lumbar spinal stenosis the doctor will usually try non-surgical treatments first. Such treatments may include anti-inflammatory medications (orally or by injection) to reduce associated swelling or analgesic drugs to control pain. Physical therapy may be prescribed with goals of improving ones strength, endurance and flexibility so that you can maintain or resume a more normal lifestyle. Spinal injections such as an epidural injection of cortisone may also be used. Such non-surgical treatments do not correct the spinal canal narrowing of lumbar spinal stenosis itself but may provide long-lasting pain control and improved life function without requiring a more invasive treatment. However, as a last resort for those patients who don't respond to non-surgical treatments, surgery will be advised.

Lumbar spinal stenosis is the most common reason for back surgery in people over the age of 50 in the United States. In 1995 it was reported that 1.2 million physician office visits were related to symptoms of lumbar spinal stenosis and this number may be closer to 2 million today. While there are various non-surgical treatments for lumbar spinal stenosis, a surgical procedure known as a laminectomy may be performed in order to reduce or eliminate the symptoms of lumbar spinal stenosis. A laminectomy or lumbar decompression surgery has the goal of opening up the bony canal to improve available space for the spinal nerves.

It is estimated that there were more than 125,000 laminectomy procedures performed for lumbar spinal stenosis in 2003 alone and this number is most likely more today. The financial impact in terms of health care dollars and lost work hours reached billions of dollars each year in this country. Rapidly expanding numbers of people over the age of 50 represent a global health care challenge without precedent and lumbosacral pain is a significant health care issue. In 2000, the number of persons aged 60 years or older was estimated at 605 million. That number is project to grow to almost 2 billion by 2050 when the population of older persons will be larger than the population of children (0-14 years) for the first time in human history.

As indicated, a laminectomy is usually a last resort for treating lumbar spinal stenosis. This is because a laminectomy is an invasive surgical procedure. It would thus be desirable to provide a surgical treatment for lumbar spinal stenosis that is less invasive than a laminectomy.

SUMMARY OF THE INVENTION

The present invention is a spinal implant or stenotic device particularly for creating spinal kyphosis and/or augmenting spinal stenosis. The spinal implant is embodied as a bony spinal protrusion spacer, spinous process spacer, interlaminar spacer, or inter-joint spacer configured to be received in and fit between bony spinal protrusions of adjacent vertebrae of the spine and hold them apart. The spinal spacer may be made of titanium, PEEK, bone, a biocompatible elastomeric or other biocompatible material or compound.

In use, the present bony spinal protrusion spacer is not fixed to any bony structures. Because the present bony spinal protrusion spacer is not fixed to any bony structures of the vertebrae, use of the present bony spinal protrusion spacer does not result in fusion. It may therefore be removed if necessary.

Attachment or placement of the present bony spinal protrusion spacer to adjacent bony spinal protrusions such as spinous processes is accomplished via retention structures formed as part of the intralaminar, spinous process or bony spinal protrusion spacer. The retention structures provide one or more ridges, bumps, protrusions, projections, lips, flanges, overhangs, overhangs that are threadably engaged, extensions and/or the like that form one or more pockets or cavities into which upper and lower bony spinal protrusions are separately lodged and held. In this manner (via retention of the bony spinal protrusion), appropriate and/or desired spacing between adjacent vertebrae is maintained. As such, the present bony spinal protrusion spacer is designed to remain safely and permanently in place without attaching to the bone or ligaments of the back.

The present bony spinal protrusion spacer may be defined by an oval, D-shaped, H-shaped, or triangular shaped body having upper and lower openings with retention structures that are designed to allow the receipt and placement of the bony spinal protrusion spacer prevent the implant from moving once implanted.

The present bony spinal protrusion spacer is surgically implanted in a minimally invasive procedure and, as such, may be an inpatient procedure. Moreover, the implantation procedure typically takes less than one hour to perform and allows patients to walk out of the surgical locale (e.g. hospital) the same day due to rapid recovery and minimal risk of systemic and local complications.

Unlike decompressive surgery/laminectomy, the procedure for implanting the present spinal spacer is completely reversible, leaving all anatomical structures intact. Thus, the implantation procedure for the present spinal spacer can be used as a first line surgical approach without compromising any therapeutic alternatives, including laminectomy.

Because extension (e.g. standing upright) provokes spinal stenosis symptoms, the present spinal implant is designed to limit extension of the lumbar spine and keep open the canal in the lower spine that carries nerves to the legs, thereby relieving symptoms. Inserted through a small incision, the present spinal implant is preferably placed posterior to neural structures to minimize the risk of neural injury. Other manners of implantation may be used.

This is somewhat a very minimally invasive procedure whereby the implant is inserted into the space between adjacent bony spinal protrusions to provide localized distraction to the lamina.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A thorough discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Figure 1:
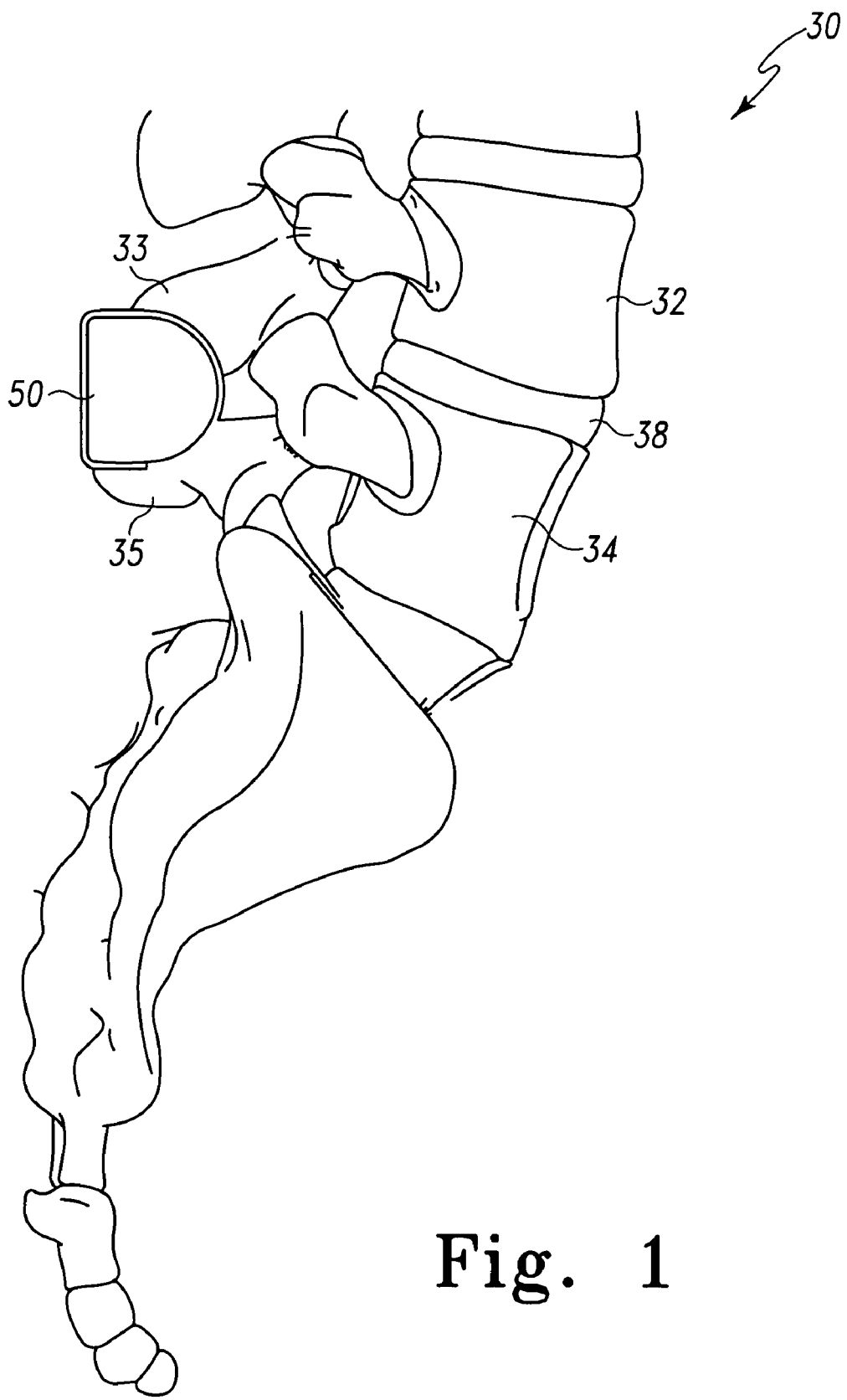
FIG. 1 is a side view of the lumbar portion of a human spine having a bony spinal protrusion spacer fashioned in accordance with the principles of the present invention, the bony spinal protrusion space shown implanted between spinous processes of adjacent lumbar vertebrae.
Figure 2:
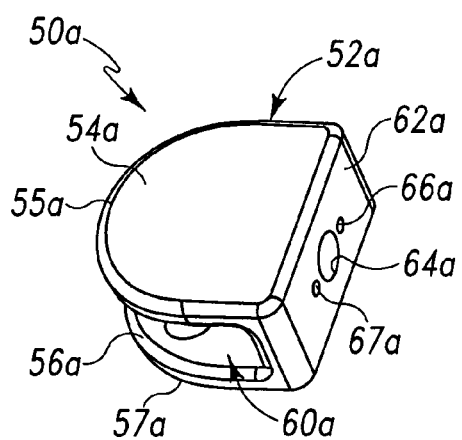
FIG. 2 is a perspective view of an exemplary embodiment of a bony spinal protrusion spacer.
Figure 3:
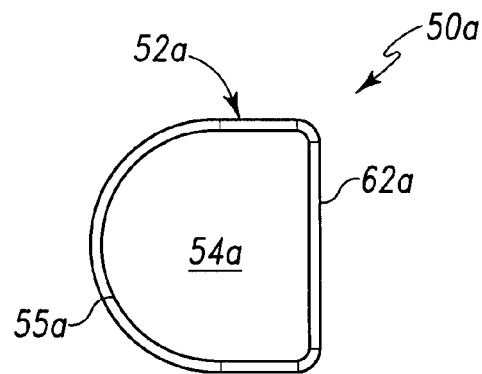
FIG. 3 is a top view of the bony spinal protrusion spacer of FIG. 2.
Figure 4:
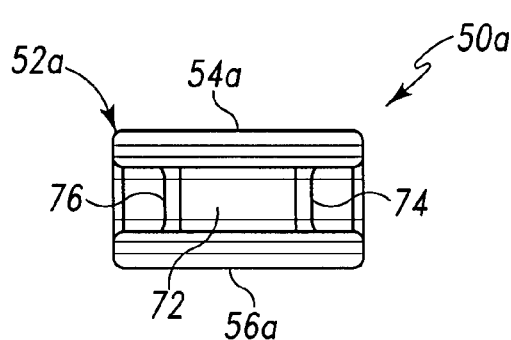
FIG. 4 is a left side view of the bony spinal protrusion spacer of FIG. 2.
Figure 5:
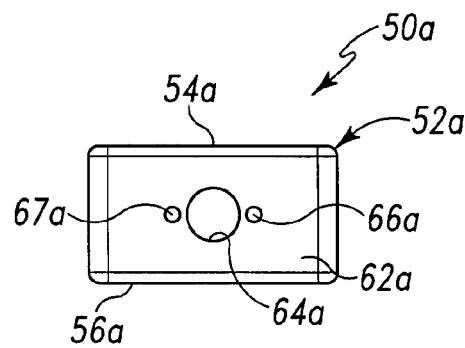
FIG. 5 is a right side view of the bony spinal protrusion spacer of FIG. 2.
Figure 6:
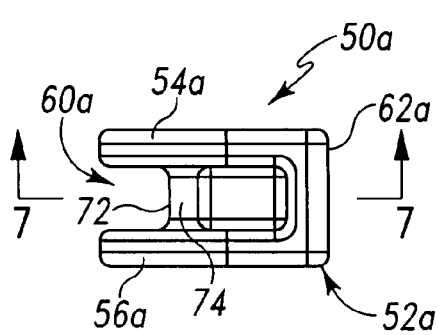
FIG. 6 is a bottom side view of the bony spinal protrusion spacer of FIG. 2.

FIG. 1 depicts the lumber region 30 of a human spine. A bony spinal protrusion spacer, spinous process spacer, interlaminar spacer, or inter-joint spacer spinous process spacer 50, representing all embodiments of a bony spinal protrusion spacer according to the principles presented herein, is shown situated between the spinous processes 33 and 35 of respective adjacent vertebrae 32 and 34. A disc 38 is naturally disposed between the vertebrae 32, 34. It should be appreciated that while the present bony spinal protrusion spacer 50 is shown situated between spinal processes 33 and 35, the present bony spinal protrusion spacer 50 may be used as an interlaminar, interbody, or interbony spinal protrusion spacer. As such, while the present bony spinal protrusion spacer 50 is shown and described in relation to the spinal processes of adjacent vertebrae, the bony spinal protrusion spacer may be used as an interlaminar, interbody or interbony spinal protrusion spacer and the principles remain the same.

The bony spinal protrusion spacer 50 is made from a biocompatible material such as titanium. Other biocompatible materials or compounds may be used such as PEEK, bone or an elastomeric. As described in greater detail below with respect to various exemplary embodiments 50a, 50b and 50c of the present bony spinal protrusion spacer 50, the bony spinal protrusion spacer 50 is configured and/or adapted to receive, hold and maintain a desired spacing between the upper spinous process 33 and the lower spinous process 35 of adjacent vertebrae 32, 34. The spacing is defined by the dimensions of the bony spinal protrusion spacer 50. As such, the bony spinal protrusion spacer 50 may be made in various sizes or dimensions to accommodate various anatomies.

FIGS. 2-7 depict one exemplary embodiment 50a of the bony spinal protrusion spacer 50. The bony spinal protrusion spacer 50a is characterized by a body 52a having a first essentially D-shaped portion or side wall 54a having a rounded periphery 55a and a second essentially D-shaped portion or side wall 56a having a rounded periphery 56a. The first and second D-shaped portions 54a, 56a transversely extend from upper and lower ends of a side portion or end wall 62a such that the first and second D-shaped portions 54a, 56a define a cavity 60a therebetween. The cavity 60a is adapted to receive the upper and lower spinous processes 33 and 35.

Figure 7:
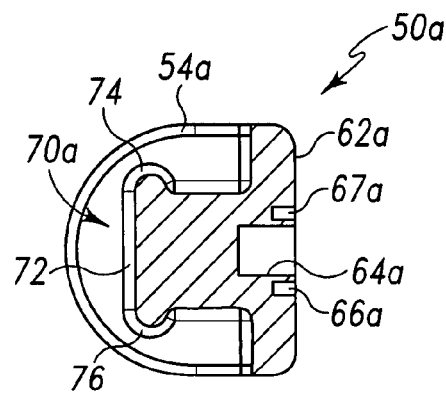
FIG. 7 is a sectional view of the bony spinal protrusion spacer of FIG. 6 taken along line 7-7 thereof.
Figure 8:
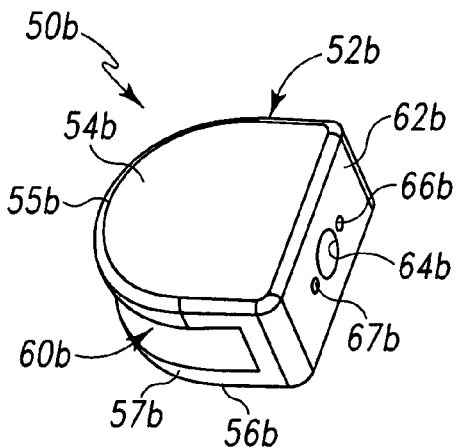
FIG. 8 is a perspective view of another exemplary embodiment of a bony spinal protrusion spacer.
Figure 9:
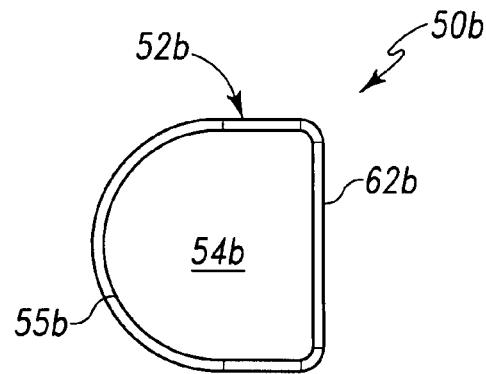
FIG. 9 is a top view of the bony spinal protrusion spacer of FIG. 3.
Figure 10:
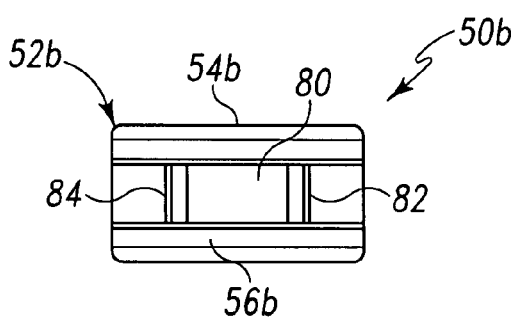
FIG. 10 is a left side view of the bony spinal protrusion spacer of FIG. 3.
Figure 11:
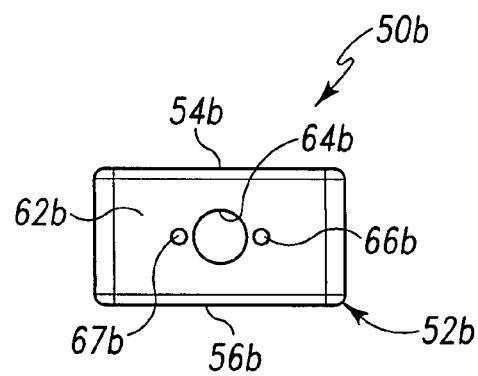
FIG. 11 is a right side view of the bony spinal protrusion spacer of FIG. 3.
Figure 12:
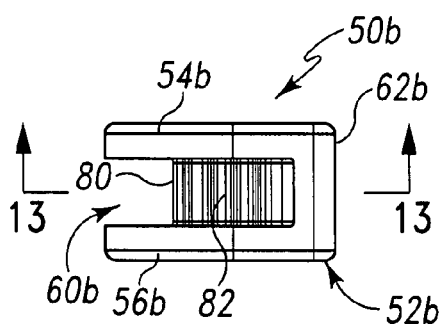
FIG. 12 is a bottom side view of the bony spinal protrusion spacer of FIG. 3.

The side portion 62a is sized such that the cavity 60a defined between the first and second D-shaped portions 54a, 56a can receive the width of the spinous processes 33, 35. As best seen in FIG. 7, the bony spinal protrusion spacer 50a has a protuberance 70a that extends from the side portion 62a and into the cavity 60a. The protuberance 70a defines a face or front 72 having first and second rounded bumps 74, 76. The bumps aid in positive insertion and retention of the spinous process spacer onto the spinous processes 33, 35. Particularly, the bumps 74 and 76 will slightly spread the spinous processes 33, 35 during insertion, but then allow the spinous processes 33, 35 to be retained between the bumps 74, 76 and the end wall of the side portion 62a. The protuberance 70a maintains spacing of the spinous processes 33, 35 while not allowing the bony spinal protrusion spacer 50a to slip out from between the spinous processes 33, 35.

The side portion 62a includes a bore 64a that may or may not be internally threaded. The bore 64a is adapted to receive an insertion tool (not shown) used to aid in inserting or implanting the bony spinal protrusion spacer bony spinal protrusion spacer bony spinal protrusion spacer process spacer 50a. Additionally, the side portion 62a includes first and second side bores 66a, 67a that are utilized as counter torque holes for insertion (implanting) of the bony spinal protrusion spacer 50a.

FIGS. 8-13 depict another exemplary embodiment 50b of the bony spinal protrusion spacer bony spinal protrusion spacer bony spinal protrusion spacer process spacer 50. The bony spinal protrusion spacer 50b is characterized by a body 52b having a first essentially D-shaped portion 54b having a rounded periphery 55b and a second essentially D-shaped portion 56b having a rounded periphery 56b. The first and second D-shaped portions 54b, 56b transversely extend from upper and lower ends of a side portion 62b such that the first and second D-shaped portions 54b, 56b define a cavity 60b therebetween. The cavity 60b is adapted to receive the upper and lower spinous processes 33 and 35.

Figure 13:
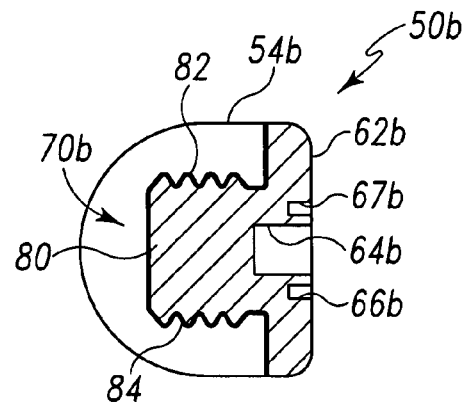
FIG. 13 is a sectional view of the bony spinal protrusion spacer of FIG. 12 taken along line 13-13 thereof.
Figure 14:
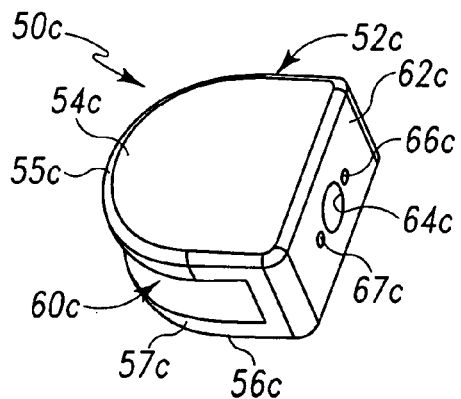
FIG. 14 is a perspective view of another exemplary embodiment of a bony spinal protrusion spacer.
Figure 15:
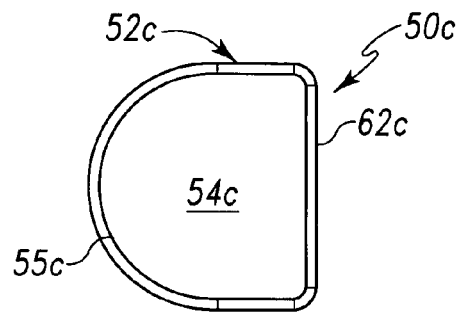
FIG. 15 is a top view of the bony spinal protrusion spacer of FIG. 14.
Figure 16:
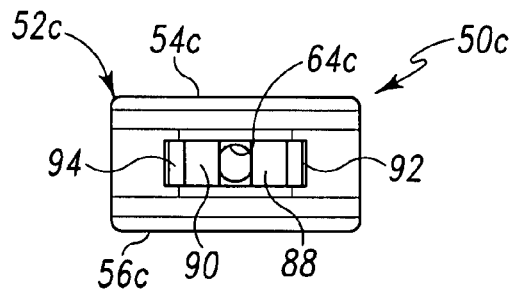
FIG. 16 is a left side view of the bony spinal protrusion spacer of FIG. 14.
Figure 17:
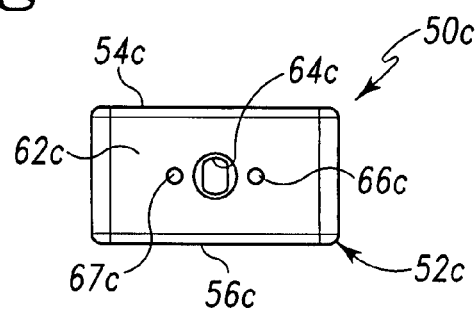
FIG. 17 is a right side view of the bony spinal protrusion spacer of FIG. 14.
Figure 18:
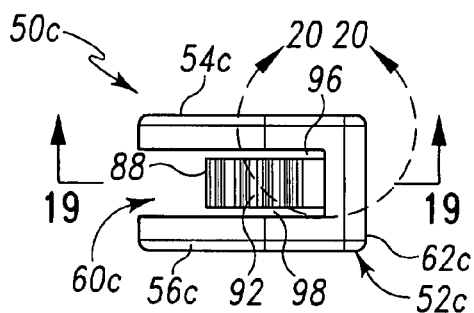
FIG. 18 is a bottom side view of the bony spinal protrusion spacer of FIG. 14.

The side portion 62b is sized such that the cavity 60b defined between the first and second D-shaped portions 54b, 56b can receive the width of the spinous processes 33, 35. As best seen in FIG. 13, the bony spinal protrusion spacer bony spinal protrusion spacer bony spinal protrusion spacer process spacer 50b has a protuberance 70b that extends from the side portion 62b and into the cavity 60b. The protuberance 70b defines a face or front 80 and serrated or toothed sides 82, 84. The serrated sides 82, 84 aid in positive insertion and retention of the spinous process spacer onto the spinous processes 33, 35. Particularly, the serrated sides 82, 84 allow the spinous processes 33, 35 to be retained thereon. The protuberance 70b maintains spacing of the spinous processes 33, 35 while not allowing the bony spinal protrusion spacer 50b to slip out from between the spinous processes 33, 35.

The side portion 62b includes a bore 64b that may or may not be internally threaded. The bore 64b is adapted to receive an insertion tool (not shown) used to aid in inserting or implanting the bony spinal protrusion spacer 50b. Additionally, the side portion 62b includes first and second side bores 66b, 67b that are utilized as counter torque holes for insertion (implanting) of the bony spinal protrusion spacer 50b.

FIGS. 14-20 depict another exemplary embodiment 50c of the bony spinal protrusion spacer bony spinal protrusion spacer bony spinal protrusion spacer process spacer 50. The bony spinal protrusion spacer 50c is characterized by a body 52c having a first essentially D-shaped portion 54c having a rounded periphery 55c and a second essentially D-shaped portion 56c having a rounded periphery 56c. The first and second D-shaped portions 54c, 56c transversely extend from upper and lower ends of a side portion 62c such that the first and second D-shaped portions 54c, 56c define a cavity 60c therebetween. The cavity 60c is adapted to receive the upper and lower spinous processes 33 and 35.

Figure 19:
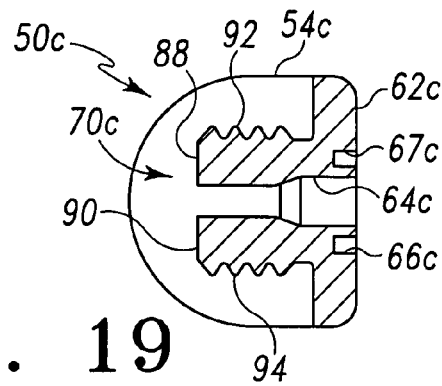
FIG. 19 is a sectional view of the bony spinal protrusion spacer of FIG. 18 taken along line 19-19 thereof.

The side portion 62c is sized such that the cavity 60c defined between the first and second D-shaped portions 54c, 56c can receive the width of the spinous processes 33, 35. As best seen in FIG. 19, the bony spinal protrusion spacer 50c has a protuberance 70c that extends from the side portion 62c and into the cavity 60c. The protuberance 70c defines a first protuberance portion 88 and a second protuberance portion 90 since bore 64c extends from the side portion 62c and through the protuberance 70c. This allows a screw to be inserted therein in order to spread the two protuberance portions 88, 90 for positive retention of the spinous processes 33, 35.

The protuberance portions 88, 90 have respective serrated or toothed sides 92, 94. The serrated sides 92, 94 aid in positive insertion and retention of the spinous process spacer onto the spinous processes 33, 35. Particularly, the serrated sides 92, 94 allow the spinous processes 33, 35 to be retained thereon. The protuberance 70c maintains spacing of the spinous processes 33, 35 while not allowing the spinous process spacer 50c to slip out from between the spinous processes 33, 35.

Figure 20:
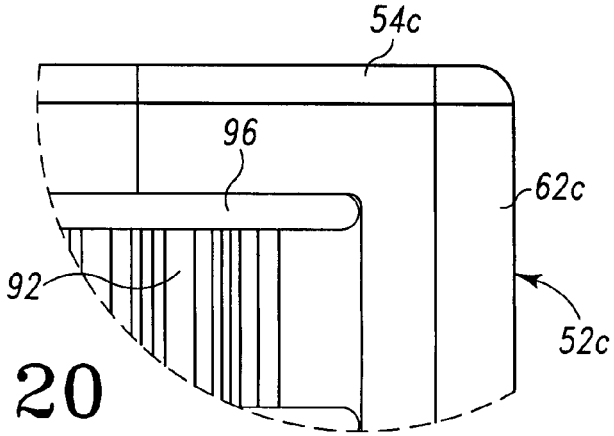
FIG. 20 is an enlarged partial view of the bony spinal protrusion spacer of FIG. 18 taken along circle 20-20 thereof.

In FIG. 20, a relief area 96 is particularly shown. The relief area 96 allows limited play or movement of the protuberance portions 88, 90 relative to the D-shaped portion 54c. A like relief area 98 is provided opposite the relieve area 98 (see FIG. 18). The relief area 98 allows limited play or movement of the protuberance portions 88, 90 relative to the D-shaped portion 56c.

The side portion 62c includes a bore 64c that may or may not be internally threaded. The bore 64c is adapted to receive an insertion tool (not shown) used to aid in inserting or implanting the bony spinal protrusion spacer 50c. Additionally, the side portion 62c includes first and second side bores 66c, 67c that are utilized as counter torque holes for insertion (implanting) of the bony spinal protrusion spacer 50c.

It should be appreciated that the bony spinal protrusion spacer 50 may come in various sizes/dimensions to accommodate various spinous process anatomies as well as provide a desired spacing therebetween. Also, the body of the bony spinal protrusion spacer 50 may be H-shaped, triangular or otherwise.

The present bony spinal protrusion spacer 50 is implanted between adjacent spinous processes through an incision made in the patient proximate the area of implantation. Adjacent vertebrae are distracted and an appropriate dimensioned bony spinal protrusion spacer 50 is situated between the adjacent spinous processes.

While the invention has been illustrated and described in detail in the drawings and foregoing description, the same is to be considered as illustrative and not restrictive in character, it being understood that only preferred embodiments have been shown and described and that all changes and/or modifications that come within the spirit of the invention are desired to be protected.

What is claimed is:

1. A spinal implant comprising:
a body having a first D-shaped portion, a second D-shaped portion spaced apart from the first D-shaped portion, a side portion, and a protuberance, wherein the side portion and the protuberance extend between the first D-shaped portion and the second D-shaped portion, wherein the protuberance includes a first bump and a second bump extending in different directions and disposed apart from the side portion;
an upper opening in the body to provide access to a first substantially enclosed cavity defined by the first D-shaped portion, the second D-shaped portion, the protuberance, the side portion, and the first bump;
a lower opening in the body to provide access to a second substantially enclosed cavity defined by the first D-shaped portion, the second D-shaped portion, the protuberance, the side portion, and the second bump;
wherein the first substantially enclosed cavity is configured to receive a portion of a first bony spinal protrusion of a first vertebra; and wherein the second substantially enclosed cavity is configured to receive a portion of a second bony spinal protrusion of a second vertebra that is adjacent to the first vertebra.

2. The spinal implant of claim 1, wherein the first bump is configured to prevent the body from moving relative to the first bony spinal protrusion, and the second bump is configured to prevent the body from moving relative to the second bony spinal protrusion.

3. The spinal implant of claim 1, wherein the body is formed of a biocompatible material.

4. The spinal implant of claim 1, wherein the upper opening faces the same direction as the first bump, and wherein the lower opening faces the same direction as the second bump.

5. A spinal implant comprising:
   a body formed of a biocompatible material the body having:
      a first side wall,
      a second side wall spaced apart from the first side wall,
      an end wall extending between the first side wall and the second side wall;
      a protuberance extending between the first side wall and the side wall,
      an attachment structure disposed in the opening and extending from the protuberance, the attachment structure having:
         a first projection extending from the protuberance in a first direction and disposed apart from the end wall, and
         a second projection extending from the protuberance in a second direction different than the first direction and disposed apart from the end wall,
      a first opening in the body to provide access to a first substantially enclosed cavity defined by the first side wall, the second side wall, the protuberance, the end wall, and the first projection;
      a second opening in the body to provide access to a second substantially enclosed cavity defined by the first side wall, the second side wall, the protuberance, the end wall, and the second projection;
      wherein the first side wall, the second side wall, the protuberance, and the attachment structure define a cavity configured to receive and retain a first bony spinal protrusion of a first vertebra and a second bony spinal protrusion of a second vertebra that is adjacent the first vertebra.

6. The spinal implant of claim 5, the first opening facing generally the same direction as the first projection, and wherein the second opening facing generally the same direction as the second projection.

7. The spinal implant of claim 5, wherein at least one of the first side wall and the second side wall is D-shaped.

8. A spinal implant comprising:
   a first portion having D-shaped surface;
   a second portion having D-shaped surface generally parallel and spaced from the first portion so as to define an interior therebetween;
   a side portion extending between the first portion and the second portion; and
   a central structure formed in the interior and configured to receive and hold a first bony spinal protrusion of a first vertebra and a second bony spinal protrusion of a second vertebra that is adjacent the first vertebra, wherein the central structure comprises a protuberance with first and second projections extending in different directions to form a first cavity to receive the first vertebra and a second cavity to receive the second vertebra;
   a first opening to provide access to a first substantially enclosed cavity defined by the first portion, the second portion, the protuberance, the side portion, and the first projection;
   a second opening in the body to provide access to a second substantially enclosed cavity defined by the first side wall, the second side wall, the protuberance, the end wall, and the second ridge.

9. The spinal implant of claim 8, wherein the central structure includes a bore configured to receive an insertion tool.

10. The spinal implant of claim 9, wherein the central structure includes a pair of side bores adjacent to the bore.

11. A method for treating spinal stenosis comprising the steps of:
   creating an opening proximate first and second stenotic vertebrae;
   spreading the first and second stenotic vertebrae; and
   inserting an implant between the first and second stenotic vertebrae, the implant configured to maintain a spacing between the first and second stenotic vertebrae and be held thereby, the implant comprising:
      a body having a first D-shaped portion, a second D-shaped portion spaced apart from the first D-shaped portion, a side portion, and a protuberance, wherein the side portion and the protuberance extend between the first D-shaped portion and the second D-shaped portion, wherein the protuberance includes a first bump and a second bump extending in different directions and disposed apart from the side portion;
      an upper opening in the body to provide access to a first substantially enclosed cavity defined by the first D-shaped portion, the second D-shaped portion, the protuberance, the side portion, and the first bump;
      a lower opening in the body to provide access to a second substantially enclosed cavity defined by the first D-shaped portion, the second D-shaped portion, the protuberance, the side portion, and the second bump;
      wherein the first substantially enclosed cavity is configured to receive a portion of a first bony spinal protrusion of a first vertebra; and
      wherein the second substantially enclosed cavity is configured to receive a portion of a second bony spinal protrusion of a second vertebra that is adjacent to the first vertebra.

* * * * *